US012741087B2

(12) United States Patent
Yang

(10) Patent No.: US 12,741,087 B2
(45) Date of Patent: Sep. 22, 2026

(54) BILATERALLY DRIVEN INTELLIGENT CONTROL INFUSION DEVICE

(71) Applicant: MEDTRUM TECHNOLOGIES INC., Shanghai (CN)

(72) Inventor: Cuijun Yang, Shanghai (CN)

(73) Assignee: MEDTRUM TECHNOLOGIES INC., Shanghai (CN)

( * ) Notice: Subject to any disclaimer, the term of this patent is extended or adjusted under 35 U.S.C. 154(b) by 736 days.

(21) Appl. No.: 17/924,350

(22) PCT Filed: May 14, 2021

(86) PCT No.: PCT/CN2021/093875
§ 371 (c)(1),
(2) Date: Nov. 9, 2022

(87) PCT Pub. No.: WO2021/228232
PCT Pub. Date: Nov. 18, 2021

(65) Prior Publication Data

US 2023/0173174 A1 Jun. 8, 2023

(30) Foreign Application Priority Data

May 14, 2020 (WO) ................ PCT/CN2020/090152

(51) Int. Cl.
*A61M 5/145* (2006.01)
*A61M 5/14* (2006.01)
(Continued)

(52) U.S. Cl.
CPC ............ *A61M 5/1452* (2013.01); *A61M 5/14* (2013.01); *A61M 5/14236* (2013.01);
(Continued)

(58) Field of Classification Search
CPC .... A61M 2205/106; A61M 2205/0266; A61M 5/482; A61M 5/31526
(Continued)

(56) References Cited

U.S. PATENT DOCUMENTS

2003/0199824 A1* 10/2003 Mahoney ............ A61M 5/1452 604/155
2008/0051710 A1* 2/2008 Moberg .............. A61M 5/1456 604/131
(Continued)

FOREIGN PATENT DOCUMENTS

CN 101208515 6/2008
CN 101208515 A * 6/2008 ........ A61M 5/14248
(Continued)

OTHER PUBLICATIONS

"International Search Report (Form PCT/ISA/210) of PCT/CN2021/093875," mailed on Jul. 29, 2021, with English translation thereof, pp. 1-5.

*Primary Examiner* — Jason E Flick
*Assistant Examiner* — Isabella S North
(74) *Attorney, Agent, or Firm* — JCIP GLOBAL INC.

(57) ABSTRACT

A bilaterally driven intelligent control infusion device, comprising: infusion unit, the infusion unit comprises a drug storage unit, a piston and a rigid screw, the piston is arranged in the drug storage unit, a metal piece arranged on the piston, fixedly connected to the rigid screw; a driving wheel, provided with wheel teeth, drives the screw movement by rotation, the screw advances the piston to move; a driving unit cooperating with the driving wheel; and a power unit, connected to the driving unit, outputs forces in two different directions on the driving unit to lead driving unit to pivot; a position detector, interacted with the metal piece to generate signal; a program unit, connected to the infusion unit, convert the received signal into the piston position informa- (Continued)

tion and can control the driving unit to operate with different infusion rate according to requirements.

15 Claims, 13 Drawing Sheets

(51) Int. Cl.

| | |
|---|---|
| ***A61M 5/142*** | (2006.01) |
| ***A61M 5/168*** | (2006.01) |
| ***A61M 5/172*** | (2006.01) |
| ***G16H 20/17*** | (2018.01) |

(52) U.S. Cl.

CPC .... *A61M 5/14244* (2013.01); *A61M 5/14248* (2013.01); *A61M 5/16804* (2013.01); *A61M 5/172* (2013.01); *G16H 20/17* (2018.01); *A61M 2005/14208* (2013.01); *A61M 2005/14506* (2013.01); *A61M 2205/0266* (2013.01); *A61M 2205/10* (2013.01); *A61M 2205/106* (2013.01); *A61M 2205/33* (2013.01); *A61M 2205/3317* (2013.01); *A61M 2205/3327* (2013.01); *A61M 2205/36* (2013.01); *A61M 2205/50* (2013.01); *A61M 2209/088* (2013.01); *A61M 2230/201* (2013.01)

(58) Field of Classification Search

USPC ........................................................... 604/65

See application file for complete search history.

(56) References Cited

U.S. PATENT DOCUMENTS

| | | | | |
|---|---|---|---|---|
| 2008/0247748 | A1* | 10/2008 | Tanimura ................ | G03B 5/00<br>396/502 |
| 2010/0081993 | A1* | 4/2010 | O'Connor ........ | A61M 5/14248<br>604/151 |
| 2019/0117881 | A1 | 4/2019 | Yang | |

FOREIGN PATENT DOCUMENTS

| | | | | | |
|---|---|---|---|---|---|
| CN | 106139311 | | | 11/2016 | |
| CN | 106139311 | A | * | 11/2016 | ........ A61M 5/14244 |
| CN | 108261585 | | | 7/2018 | |
| CN | 111939386 | | | 11/2020 | |
| CN | 112237655 | | | 1/2021 | |
| JP | 2000110709 | A | * | 4/2000 | |
| JP | 2000112526 | A | * | 4/2000 | |
| JP | 2006132580 | A | * | 5/2006 | |
| JP | 2011027003 | A | * | 2/2011 | |

* cited by examiner

100
Up
110a
20
$l_1$
$\alpha$
$l_2$
Down
110b

BILATERALLY DRIVEN INTELLIGENT CONTROL INFUSION DEVICE

CROSS-REFERENCE TO RELATED APPLICATION

This application is a 371 of international application of PCT application serial no. PCT/CN2021/093875, filed on May 14, 2021, which claims the priority benefit of PCT application serial no. PCT/CN2020/090152, filed on May 14, 2020. The entirety of each of the above-mentioned patent applications is hereby incorporated by reference herein and made a part of this specification.

TECHNICAL FIELD

The present invention mainly relates to the field of medical instruments, in particular to a bilaterally driven intelligent control infusion device and closed-loop artificial pancreas.

BACKGROUND

The pancreas in a normal person can automatically monitor the amount of glucose in the blood and automatically secrete the required dosage of insulin/glucagon. However, for diabetic patients, the function of the pancreas is abnormal, and the pancreas cannot normally secrete required dosage of insulin. Therefore, diabetes is a metabolic disease caused by abnormal pancreatic function and also a lifelong disease. At present, medical technology cannot cure diabetes, but can only control the onset and development of diabetes and its complications by stabilizing blood glucose.

Patients with diabetes need to check their blood glucose before injecting insulin into the body. At present, most of the detection methods can continuously detect blood glucose, and send the blood glucose data to the remote device in real time for the user to view. This detection method is called Continuous Glucose Monitoring (CGM), which requires the detection device to be attached to the surface of the patients' skin, and the sensor carried by the device is inserted into the subcutaneous tissue fluid for testing. According to the blood glucose (BG) level, the infusion device, as a closed-loop or semi-closed-loop artificial pancreas, injects the currently required insulin dose. At present, the detection device and the infusion device are connected to each other to form a closed-loop artificial pancreas with the processing of the program unit.

A bilaterally driven intelligent control infusion device is a medical device that achieves treatment of a patient's physiological condition by continuously injecting a drug into a patient. Bilaterally driven intelligent control infusion device is widely used for the treatment of diabetes, allowing required doses of insulin to be continuously infused into the subcutaneous tissue of the patient's body, thereby simulating the secretion function of the pancreas, thereby keeping the patient's blood sugar stable. The drug fluid is usually stored inside the infusion pump. The existing bilaterally driven intelligent control infusion device usually attaches the pump body directly to the patient's body through a medical adhesive tape, and the patient operates a remote device to control infusion.

In the case of drug infusion, the current infusion devices can only operate with one infusion rate, therefore, the infusion process cannot be flexibly controlled, and the infusion efficiency is relatively low. Moreover, the minimum dose that can be infused each time is relatively large, which can cause the concentration of some substance(s) in a patient's body fluid to fluctuate greatly under the control of the infused drug, and cannot achieve the purpose of more accurately controlling the concentration of that substance(s).

Therefore, there is a need in the prior art for a bilaterally driven intelligent control infusion device and closed-loop artificial pancreas that can flexibly control a drug infusion process and improve drug infusion efficiency.

BRIEF SUMMARY OF THE INVENTION

The embodiment of the invention discloses a bilaterally driven intelligent control infusion device and closed-loop artificial pancreas, can be operated with multiple infusion rate, which improves the flexibly of the infusion process, and the driving unit has multiple-mode operation, thus realizing driving the driving wheel in multiple-mode rotations and making the infusion device have multiple infusion increments or infusion rates. The patient can flexibly control the infusion process, which improves the infusion efficiency.

The invention discloses a bilaterally driven intelligent control infusion device, comprising: infusion unit, the infusion unit comprises a drug storage unit, a piston and a rigid screw, the piston is arranged in the drug storage unit, a metal piece arranged on the piston, fixedly connected to the rigid screw; a driving wheel, provided with wheel teeth, drives the screw movement by rotation, the screw advances the piston to move; a driving unit cooperating with the driving wheel; and a power unit, connected to the driving unit, outputs forces in two different directions on the driving unit to lead driving unit to pivot; a position detector, interacted with the metal piece to generate signal; a program unit, connected to the infusion unit, convert the received signal into the piston position information and can control the driving unit to operate with different infusion rate according to requirements.

According to one aspect of the present invention, the rigid screw is a metal screw, and the metal piece is electrically connected with the metal screw, so that the metal piece and the corresponding position detector constitute a capacitor, and the linear movement of the metal piece causes a change in capacitance making the corresponding position detector generate an electrical signal.

According to one aspect of the present invention, the metal piece is a magnetic metal piece, and the position detectors are magnetic induction detectors, the linear movement of the magnetic metal piece causes a change in the magnetic field around each position detector making each position detector generate a magnetic signal.

According to an aspect of the present invention, the multiple-mode operation of the driving unit includes the movement amplitude or the movement rate, therefore, the different multiple-mode operations of the driving unit include multiple different movement amplitudes or multiple different movement rates.

According to an aspect of the present invention, it further includes a pivot shaft, and the driving unit includes at least two driving arms, and the driving unit pivots around the pivot shaft to drive driving arms to move.

According to an aspect of the present invention, the driving wheel includes at least two sub-wheels, and the driving arm rotates the driving wheel by engaging the wheel teeth.

According to an aspect of the present invention, the pivot shaft is disposed between the two sub-wheels, one or more driving arms are respectively disposed on both sides of the driving unit, and each sub-wheel cooperates with at least one driving arm.

According to an aspect of the present invention, one movement amplitude corresponds to one kind of pivot mode of the driving unit, and the driving unit, pivoting in various pivot modes, drives the driving arm to rotate the driving wheel to implement increment-adjustable infusion, and each increment-adjustable infusion corresponds to an infusion increment.

According to an aspect of the present invention, multiple-mode pivot of the driving unit includes: after pivoting one or more steps in one direction in a single time, the driving unit starts pivoting one or more steps in another direction until the end of the pivot in this direction, the driving unit completes an alternate pivot in both directions to perform multiple-mode driving on the driving wheel.

According to an aspect of the present invention, the wheel teeth are ratchet teeth, and during the whole process of driving unit pivoting in one direction, the driving unit alternately pivots and stops for multiple times to drive driving arms to alternately engage and stop engaging the ratchet teeth, so that the driving wheel alternately rotates and stops rotation to perform tooth number adjustable rotation.

According to an aspect of the present invention, when the driving unit drives the driving wheel, at least one of the driving arms on one side engages the wheel teeth, while the driving arm on the other sides of the driving unit slide on the wheel teeth.

According to an aspect of the present invention, it further includes a base on which the driving wheel is movably assembled, and the base and the driving wheel are frictional fit, and the driving wheel stops rotating when the driving arm is sliding on the surface of the wheel teeth.

According to an aspect of the present invention, it further includes a position limited member which is movably assembled on the base to limit the position of the driving wheel, and the position limited member and the driving wheel are frictional fit, and the driving wheel stops rotating when all of the driving arms are sliding on the surface of the wheel teeth.

The invention also discloses a closed-loop artificial pancreas, comprising the above bilaterally driven intelligent control infusion device; and a detection unit, configured to detect blood glucose continuously, connected with the program unit and infusion unit of the infusion device.

According to an aspect of the present invention, any two of the detection unit, the program unit and the infusion unit are connected to each other configured to form a single structure whose attached position on the skin is different from the third unit.

According to an aspect of the present invention, the detection unit, the program unit and the infusion unit are connected together configured to form a single structure which is attached on only one position on the skin.

Compared with the prior art, the technical solution of the present invention has the following advantages:

In the bilaterally driven intelligent control infusion device and closed-loop artificial pancreas disclosed by the present invention, comprise a position detector, can interacted with metal piece to generate signal, and the program unit can convert the signal into the piston position information, then control the driving unit to operate with different infusion rate according to requirements, which improves the flexibly of the infusion process and infusion efficiency significantly.

Furthermore, the power unit outputs forces in two different directions on the driving unit to lead driving unit to perform multiple-mode operation, making the infusion device have multiple infusion increments or infusion rates. The driving unit has a variety of different pivot amplitudes, that is, the driving unit can realize multiple-mode pivot, thereby achieving increment-adjustable infusion. At the same time, this invention also reduces the minimum drug infusion dosage, accurately controls the process of the drug infusion, effectively avoids large fluctuations of concentration of some substance(s) in patient's body fluid and enables the patients or artificial pancreas to control and manage their physiological condition more precisely.

Furthermore, multiple-gear positions pivot of the driving unit includes: after pivoting one or more gear positions in one direction in single time, the driving unit starts pivoting one or more gear positions in another direction until the end of the pivot in this direction, the driving unit completes an alternate pivot in both directions. When a plurality of pivoting gear positions are set, the driving unit can select the pivot mode of different gear positions according to actual needs, driving the driving wheel to rotate in multiple-gear positions, thereby completing the multiple-gear positions infusion of the device, and patient or artificial pancreas can control the infusion process more flexibly.

Furthermore, in the solution of the present invention, during the whole process of the driving unit pivoting in one direction, the driving unit alternately pivots and stops in an adjustable way to drive the driving arms to alternately engage and stop engaging the ratchet teeth, so that the driving wheel alternately rotates and stops rotation to perform tooth number adjustable driving on the driving wheel. In a single rotation in one direction, adjustable pivoting of the driving unit helps delivering the infused drug in several steps by means of a pivot-stop-pivot-stop- . . . -pivot-stop alternating method to achieve accurate infusion.

Furthermore, multiple-mode pivot of the driving unit includes large mode and small mode. Patients or artificial pancreas can freely choose and switch large mode or small mode infusion according to the actual infusion volume and infusion rate requirements, making the infusion process more flexible and controllable, greatly improving the infusion efficiency.

Furthermore, a plurality of movement modes of the driving unit further comprise: one or more intermediate modes. Setting intermediate modes provides more infusion options for the patient or artificial pancreas and the patient's control of the infusion process is more flexible.

Furthermore, the infusion device further includes a base which is frictional fit with the driving wheel. The driving wheel stops rotating when the driving arm is sliding on the surface of the wheel teeth, improving the accuracy of drug infusion and eliminating potential safety hazards.

DETAILED DESCRIPTION

Figures 1A, 1B:
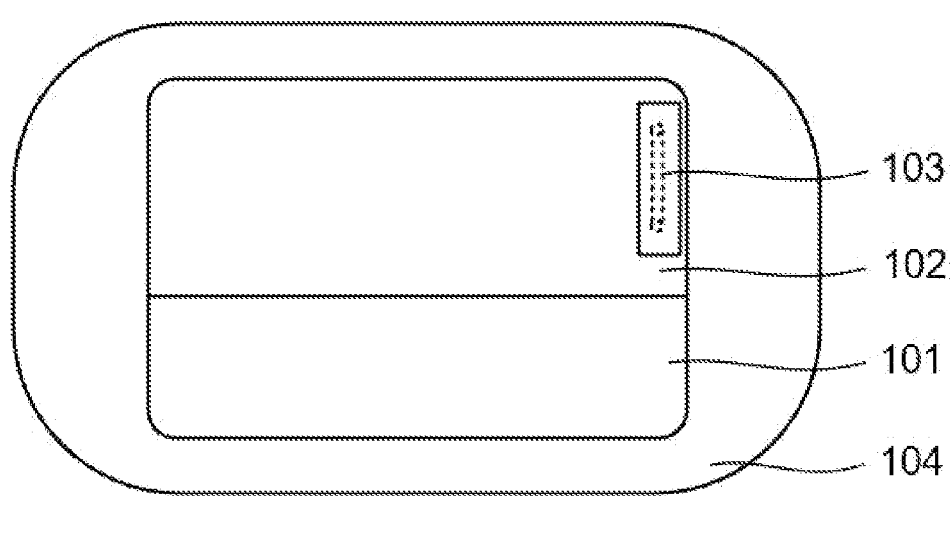
FIG. 1*a* is a schematic structural diagram of a separate design of a program unit and an infusion unit according to an embodiment of the present invention.
FIG. 1*b* is a schematic structural diagram of an integrated design of a program unit and an infusion unit according to another embodiment of the present invention.

As previously mentioned, prior art infusion devices have only one infusion rate in infusion mode and do not have the flexibility to control the infusion process.

It has been found through research that the above mentioned problems are caused by the fact that the driving unit in the prior art infusion device has only one operating mode (or only one pivot mode), which results in a relatively simple control of the infusion process in the prior art.

In order to solve this problem, the present invention provides a bilaterally driven intelligent control infusion device in which a driving unit has multiple-mode operation to perform tooth-number adjustable driving on the driving wheel. The different options of increment allow patients to flexibly control the drug infusion process. At the same time, the minimum drug infusion amount of the infusion device is effectively reduced, and the fluctuation of concentration of some substance(s) in patient's body fluid is mitigated.

Various exemplary embodiments of the present invention will now be described in detail with reference to the drawings. The relative arrangement of the components and the steps, numerical expressions and numerical values set forth in the embodiments are not to be construed as limiting the scope of the invention.

In addition, it should be understood that, for ease of description, the dimensions of the various components shown in the figures are not necessarily drawn in the actual scale relationship, for example, the thickness, width, length or distance of certain units may be exaggerated relative to other structures.

The following description of the exemplary embodiments is merely illustrative, and is not intended to be in any way limiting the invention and its application or use. The techniques, methods and devices that are known to those of ordinary skill in the art may not be discussed in detail, but such techniques, methods and devices should be considered as part of the specification.

It should be noted that similar reference numerals and letters indicate similar items in the following figures. Therefore, once an item is defined or illustrated in a drawing, it will not be discussed further in the following description of the drawings.

FIG. 1*a* and FIG. 1*b* are schematic top structural diagrams of a bilaterally driven intelligent control infusion device according to one embodiment of the present invention.

The bilaterally driven intelligent control infusion device includes an adhesive patch 104, program unit 101, infusion unit 102 and infusion needle 103.

The program unit 101 is used for controlling drug infusion, controlling power output of the power unit, receiving signals from position detector(s), establishing wireless communication with remote devices, and the like. In the embodiment of the present invention, the program unit 101 can also select different driving portions to push the wheel teeth to achieve different infusion rates, which will be described in detail below.

The infusion unit 102 includes various units for realizing the mechanical function for drug infusion, which will be described in detail below.

In the embodiment of the present invention, the program unit 101 and the infusion unit 102 are designed separately and connected by a waterproof plug. The program unit 101 can be reused, while the infusion unit 102 can be discarded after a single use. In another embodiment of the present invention, the infusion unit 102 and the program unit 101 are disposed inside the same housing 10 and connected by a wire, which both units will be discarded together after a single use, as shown in FIG. 1*b*.

The adhesive patch 104 is used to attach the infusion unit 102 or the program unit 101, or both of them to the skin surface as a whole.

One end of the infusion needle 103 is connected to the outlet of the drug storage unit, while the other end pierces the skin to infuse the drug subcutaneously. In the embodiment of the present invention, the infusion needle 103 is disposed at one end of the infusion unit 102. In other embodiments of the present invention, the infusion needle 103 may be disposed at other positions according to its functions or structural features of the device, such as being disposed at the middle portion of the device, which is not specifically limited herein. The infusion needle 103 is a rigid infusion needle or a flexible infusion needle, or designed according to its different positions and functions, the design of infusion needle 103 can also adopt a combination of rigid infusion needle(s) and flexible infusion needle(s), which is not specifically limited herein. Preferably, in the embodiment of the present invention, the infusion needle 103 is a rigid infusion needle.

Figure 2:
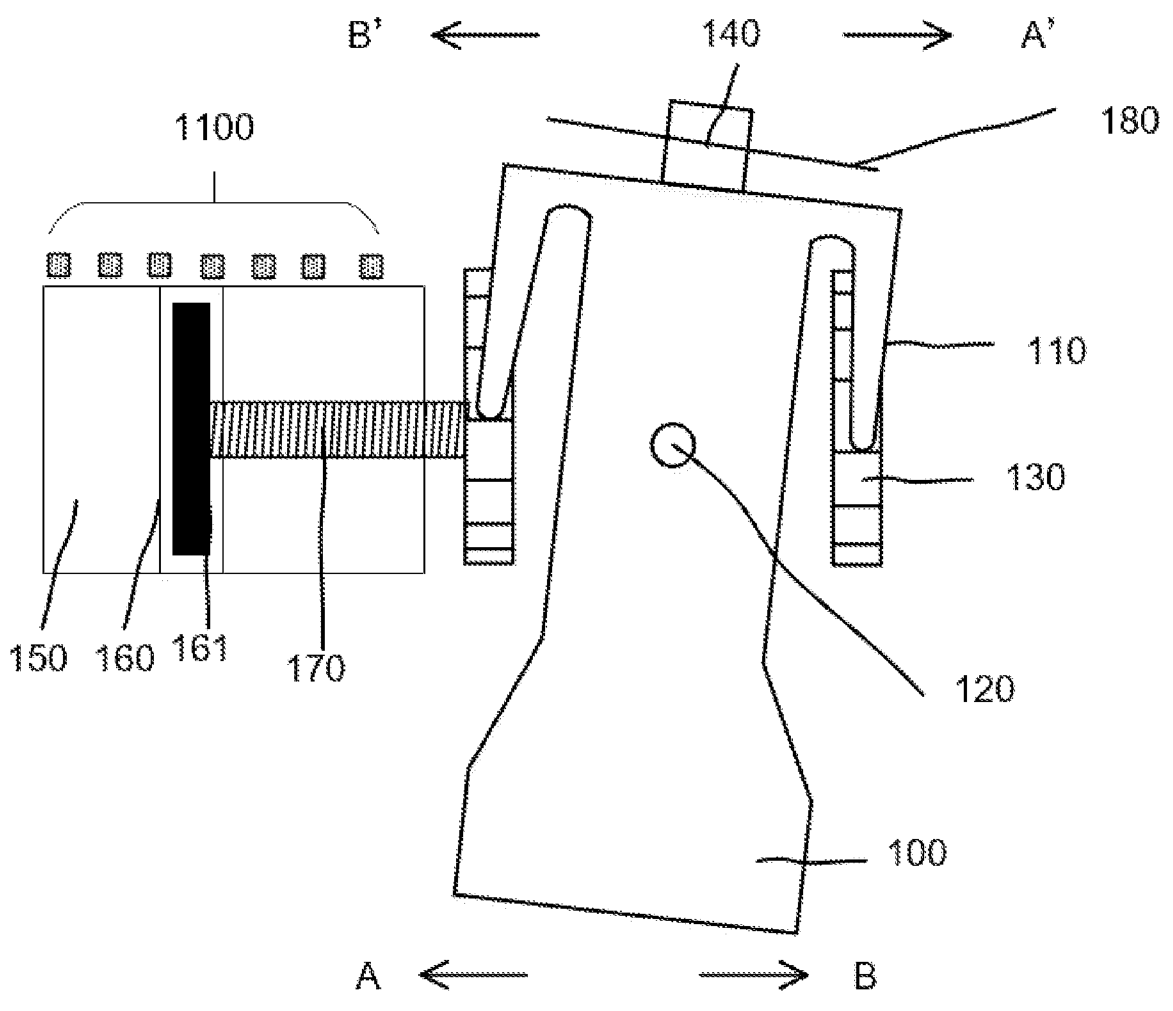
FIG. 2 is a schematic structural diagram of main structure in a bilaterally driven intelligent control infusion device according to an embodiment of the present invention.

FIG. 2 is a schematic structural diagram of main structure in a bilaterally driven intelligent control infusion device includes a driving unit 100, a driving wheel 130, a drug storage unit 150, a piston 160, a metal piece 161, a position detector 1100, a screw 170, and a power unit 180.

The screw 170 is coupled to the piston 160 and the driving wheel 130, respectively. In the embodiment of the present invention, the driving wheel 130 is movably mounted on the device base 190, and the driving wheel 130 moves the driving screw 170 through rotation to advance the piston 160 disposed in the drug storage unit 150 to move forward for the purpose of injecting drugs.

The driving unit 100 cooperates with the driving wheel 130. Here, the cooperation means that the movements of both the driving unit 100 and the driving wheel 130 are interrelated to each other.

Figure 9:
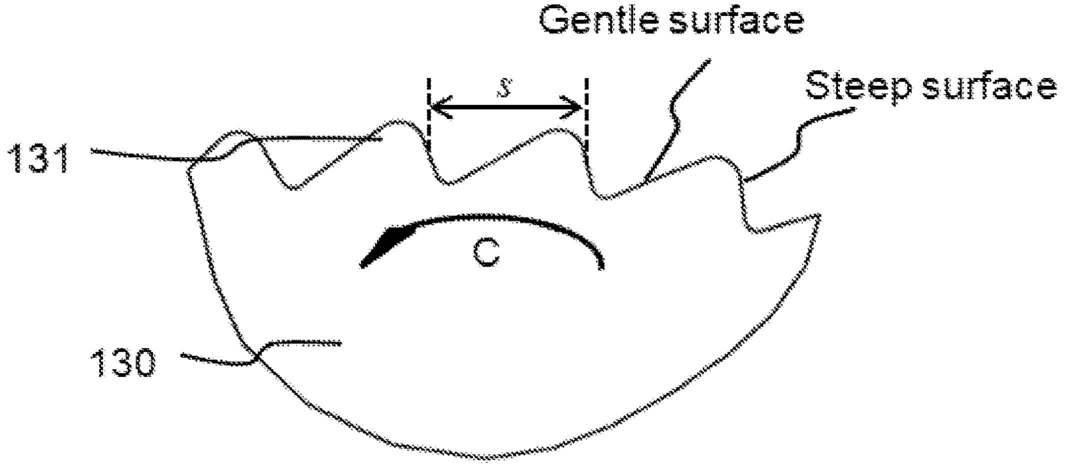
FIG. 9 is a partial schematic structural view of a driving wheel in a bilaterally driven intelligent control infusion device according to an embodiment of the present invention.
Figure 10:
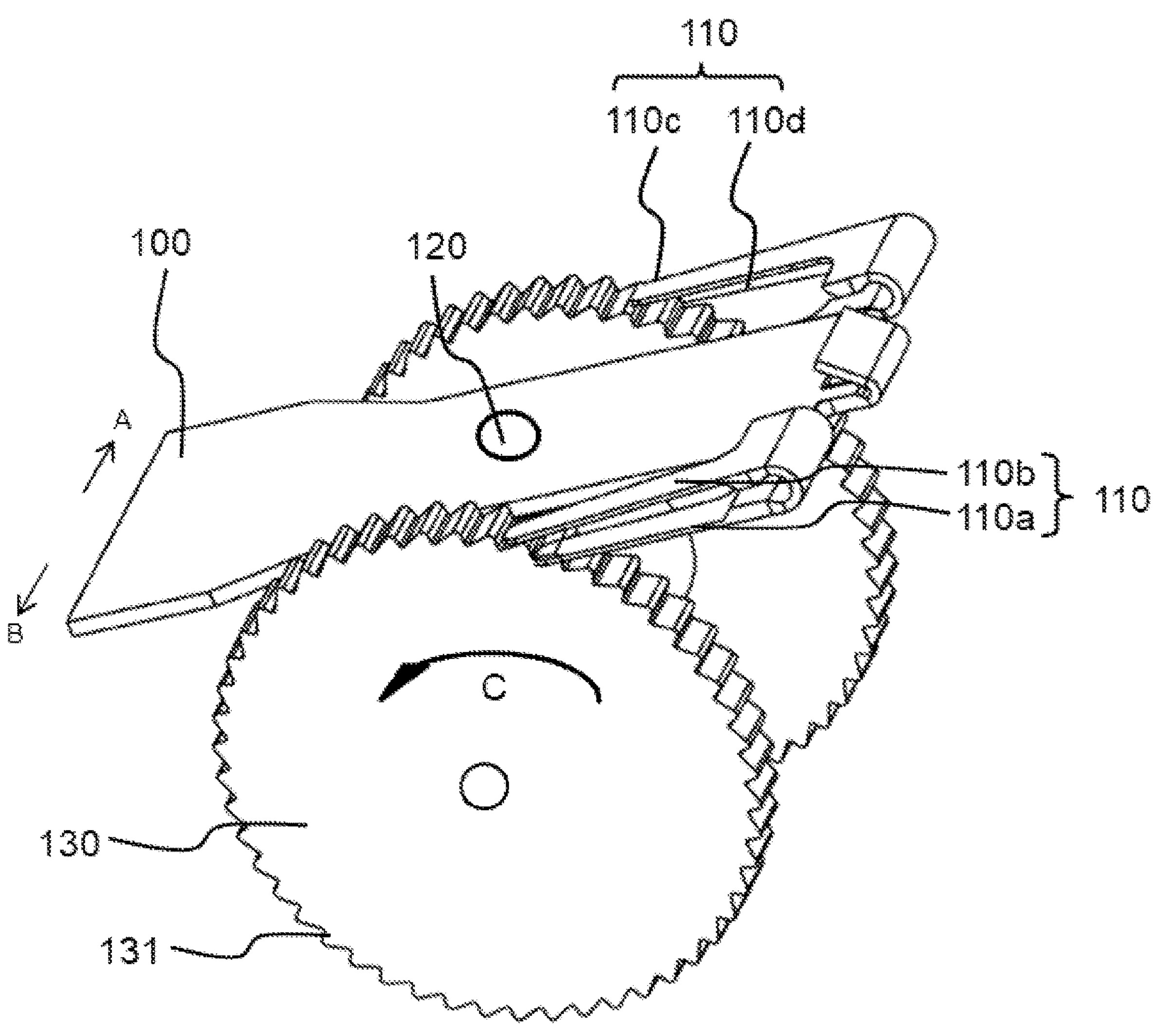
FIG. 10 is a schematic structural view of a driving unit engaging a driving wheel in a bilaterally driven intelligent control infusion device according to an embodiment of the present invention.

In the embodiment of the present invention, the driving wheel 130 is provided with wheel teeth 131 (as shown in FIG. 9 and FIG. 10). The driving unit 100 is movably connected to the base 190 through a pivot shaft 120, and the driving unit 100 can pivot around the rotating shaft 120. The driving unit 100 includes at least two driving arms 110. The pivoting driving unit 100 drives the driving arm 110 to engage the wheel teeth 131 forward to rotate the driving wheel 130. The power unit 180 outputs two different directional forces on the driving unit 100, making the driving unit 100 pivot.

Figure 3:
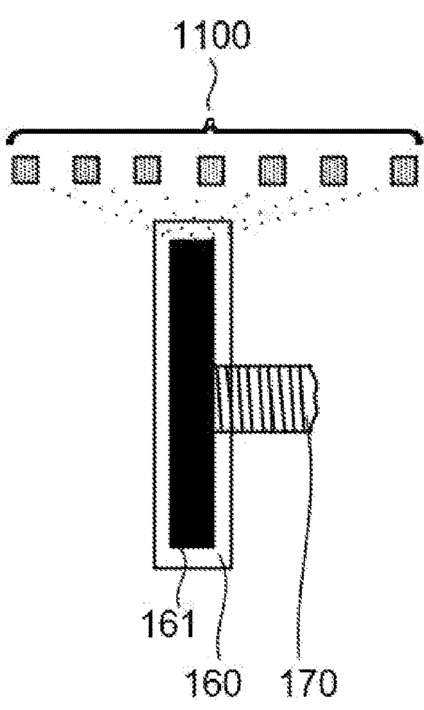
FIG. 3 is a schematic structural diagram of a metal piece and a position detector according to an embodiment of the present invention.

FIG. 3 is a schematic structural diagram of a metal piece 161 and a position detector 1100 according to an embodiment of the present invention.

The miniature patch-type intelligent control infusion device according to the embodiment of the present invention further includes one or more position detectors 1100. The position detector 1100 interacts with the metal piece 161 to detect the position of the metal piece 161, and thereby determine the position of the piston 160 to calculate the remaining amount of drug in the drug storage unit 150. Specifically, in the embodiment of the present invention, the metal piece 161 is a magnetic metal piece, and the position detector 1100 is magnetic position detector. When the metal piece 161 is located at a certain position, the location of every position detector 1100 has a certain magnetic field size and direction, allowing the position of the piston 160 to be accurately detected. When the piston 160 is moving, the magnitude and direction of the magnetic field at the location of every position detector 1100 changes accordingly, in which way the position of the piston 160 is detected in real time. The position detector 1100 sends magnetic signal(s) or magnetic signal change to the program unit 101. After processed, the signal is converted into position information of the piston 160, which is then used to calculate the remaining drug amount.

According to the specifications of the drug storage unit 150, the number of the position detectors 1100 can be one, two or more. Specifically, in the embodiment of the present invention, the number of the position detectors 1100 is seven. In another embodiment of the present invention, the number of the position detectors 1100 is two. In still another embodiment of the present invention, only one position detector 1100 is provided.

It should be noted that when there are more than two position detectors 1100, preferably, the position detectors 1100 are linearly and equally spaced. The position detector 1100 can be disposed in the infusion unit 102, or at a position, corresponding to the changing position of the piston 160, in the program unit 101, or embedded in the side wall of the drug storage unit 150, or located on the inner surface of the drug storage unit 150. The position detectors 1100 may also be arranged in other ways, which are not specifically limited herein, as long as the conditions for detecting the position of the piston 160 can be satisfied.

As previously mentioned, the rigid screw 170 only moves along its own axial direction without rotating. Therefore, the metal piece 161, embedded in the piston 160 and fixedly connected to the rigid screw 170, can also be advanced non-rotating only along the axial direction of the rigid screw 170. Compared with detecting position with a rotating screw, the embodiment of the present invention only detects magnetic field signal(s) in one-dimensional axial direction or two-dimensional plane (determined by the moving direction of the screw and a detector). The detecting principle, the operation and structural design are much simpler, and the position information is more accurate, reducing the cost of design and production.

Figure 4:
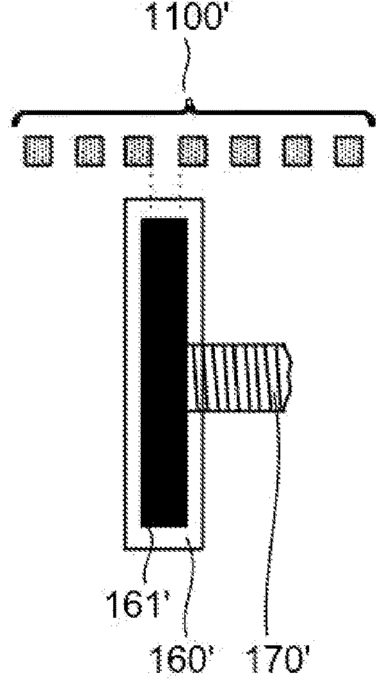
FIG. 4 is a schematic structural diagram of a metal piece and a position detector according to another embodiment of the present invention.

FIG. 4 is a schematic structural diagram of metal piece 161' and position detector 1100' according to an embodiment of the present invention.

In the embodiment of the present invention, the rigid screw 170' is made of metallic material. The metal piece 161' is fixedly and electrically connected to the rigid screw 170'. At a certain position, the metal piece 161' and a corresponding position detector 1100' will form a capacitor to generate electrical signal(s). When the piston 160' moves, the capacitance changes with the area of the electrode plate, and the corresponding position detector 1100' generates a changed electrical signal to accurately detect the position of the piston 160'. The corresponding position detector 1100' transmits the electrical signal to the program unit to be converted to the position information of the piston 160'. And then the program unit outputs the remaining drug amount. Specifically, in the embodiment of the present invention, for accurate position detection, a plurality of position detectors 290 are provided, and the setting manner thereof is as described above.

In one embodiment of the present invention, the power unit 180 outputs two different directional forces on the driving unit 100, making the driving unit 100 have different multiple-mode operation. Here, the operation mode includes the amplitude or rate of the movement. Therefore, the multiple-mode operation of the driving unit 100 includes various movement amplitudes or movement rates, which will be described in detail below.

Specifically, in the embodiment of the present invention, the power unit 180 is fixedly connected at the top position 140 of the driving unit 100, thereby dividing the power unit 180 into two left and right portions, such as the A' direction portion and the B' direction portion in FIG. 2. The driving unit 100 is alternately led to pivot in the A' direction or the B' direction through the pivot shaft 120. Specifically, in the embodiment of the present invention, when the power unit 180 leads the driving unit 100 to A' direction, the driving unit 100 pivots in A direction through the pivot shaft 120. When the power unit 180 leads the driving unit 100 in the B' direction, the driving unit 100 pivots in B direction through the pivot shaft 120. By alternately leading the driving unit 100 in A' direction and B' direction, the driving unit 100 can alternately pivot through the pivot shaft 120 in the A direction and the B direction.

Specifically, in the embodiment of the present invention, the power unit 180 is made of shape memory alloy. The A' direction portion and the B' direction portion of the shape memory alloy are alternately powered on and off, and a leading force is applied to the driving unit 100 by a change in the length of the power unit 180 thereof. The power unit 180 may be composed of one piece of shape memory alloy, or may be composed of left and right segments (such as the A' direction segment and the B' direction segment) of shape memory alloy, and is not specifically limited herein, as long as the force can be applied to lead the driving unit 100 pivot.

Here, it should be noted that the power unit 180 includes but is not limited to a shape memory alloy. In other embodiments of the present invention, the power unit 180 may also be other structures, and the location where the power unit 180 applies force to the driving unit 100 is also not limited to the top position 140, as long as the action of applying a force to the driving unit 100 can be satisfied to cause the driving unit 100 to alternately pivot left and right.

Obviously, by controlling the magnitude of the power output by the power unit 180, the driving unit 100 will have various movement amplitudes. As in the embodiment of the present invention, by controlling the magnitude of the current, the length of the shape memory alloy will change, changing the magnitude of the power and the movement amplitude of the driving unit 100. Therefore, the driving unit 100 has various movement amplitudes. One movement amplitude of the driving unit 100 corresponds to one kind of pivot mode, and therefore, the driving unit 100 has multiple-mode pivot.

Similarly, by controlling the frequency of the power output by the power unit 180, the driving unit 100 will have various movement rates. As in the embodiment of the present invention, by changing the energization frequency, the frequency of the power output also changes, thus changing the movement rate of the driving unit 100 accordingly.

Figures 5A, 5B:
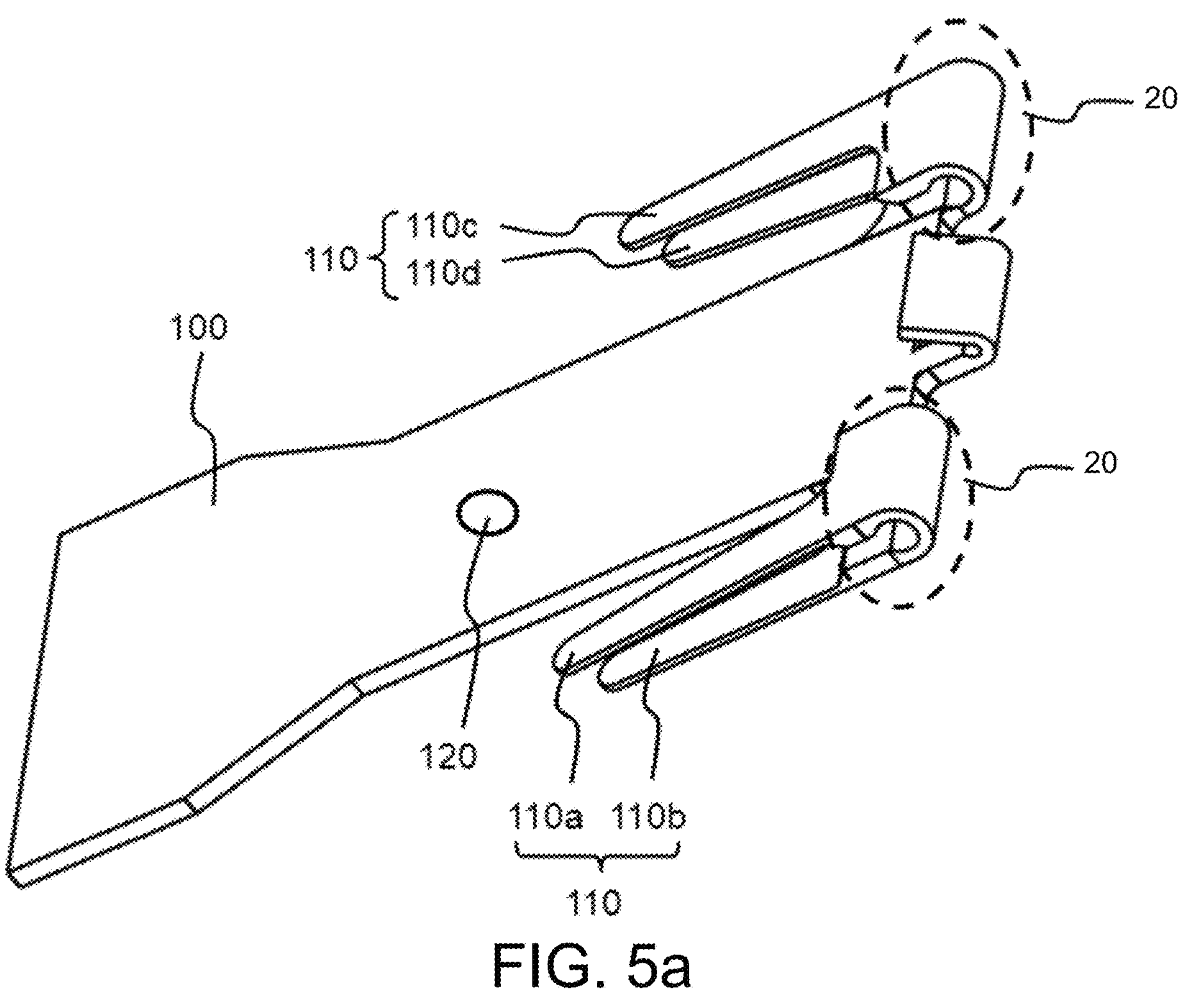
FIG. 5*a*-FIG. 5*c* are respectively a schematic structural view of a three-dimensional structure, a side view and a top view of a driving unit in a bilaterally driven intelligent control infusion device according to an embodiment of the present invention.

Referring to the perspective view of the driving unit 100 shown in FIG. 5*a*, the driving unit 100 further includes more than two driving arms 110. The driving wheel 130 includes a plurality of sub-wheels. Referring to the structure shown in FIG. 1 and FIG. 5*a*, when a plurality of driving arms 110 are installed on one side of the driving unit 100, the driving unit 100 can drive the driving arms 110 to engage the wheel teeth 131 through adjustable pivoting to rotate the driving wheel 130 by an optional number of teeth. Thus, in an embodiment of the invention, the driving unit 100 and the driving wheel 130 are designed to work compatibly, which means that the position of the driving wheel 130 and the number of the sub-wheels need to be compatible with the working principle of the driving unit 100 and the number, position and structure of the driving arms 110.

As shown in FIG. 1 and FIG. 5*a*, in the embodiment of the present invention, a plurality of driving arms 110 are installed on each side of the driving unit 100. Therefore, a plurality of sub-wheels are also installed on both sides of the driving unit 100 to cooperate with the driving arms 110. Specifically, in the embodiment of the present invention, the driving unit 100 includes four driving arms 110, which are 113*a*, 113*b*, 110*c*, and 110*d*, respectively. 113*a*, 113*b* are installed on one side of the driving unit 100, while 110*c*, 110*d* are installed on the other side of the driving unit 100. The driving wheel 130 includes two sub-wheels, one of which cooperates with 113*a*, 113*b* and the other of which cooperates with 110*c*, 110*d*.

It should be noted that the driving wheel 130 may further include more than two sub-wheels. For example, according to the design of the position and structure of the plurality of driving arms 110, two adjacent sub-wheels may be set on one side of the driving unit 100 to cooperate with different positions, numbers of driving arms 110 on this side of the driving unit 100.

Figure 5C:
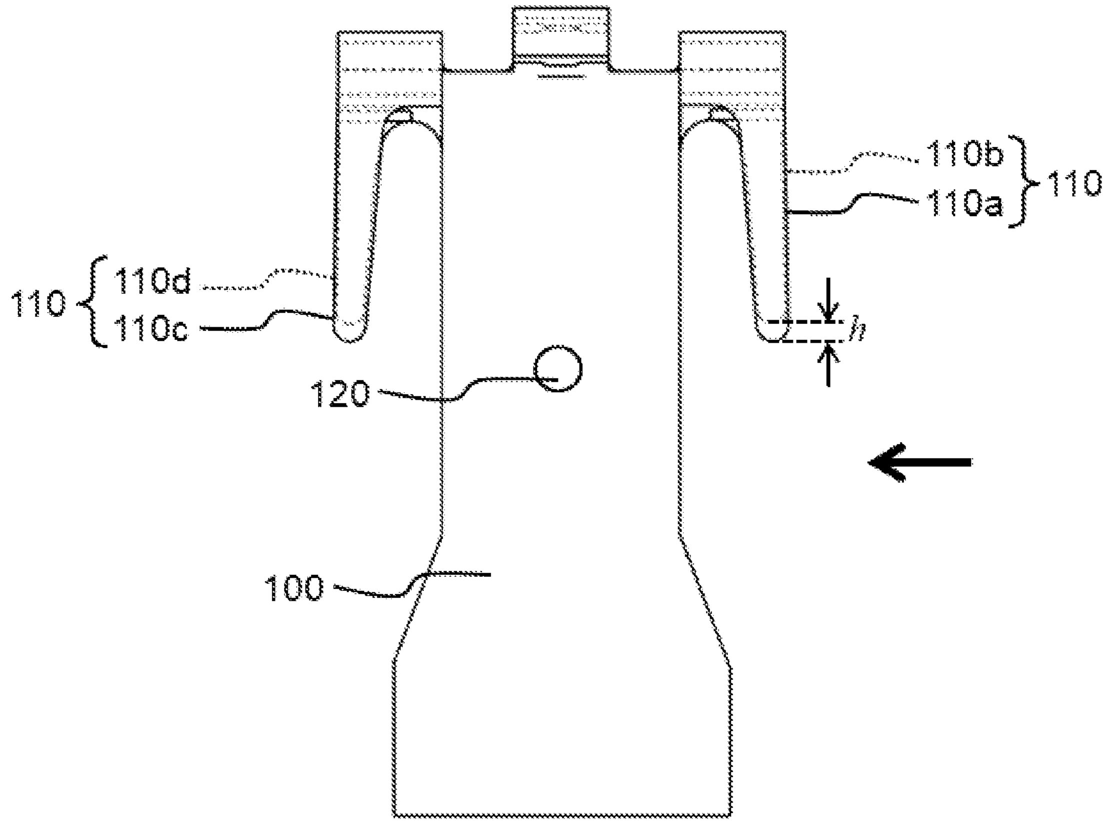

FIG. 5*a*, FIG. 5*b*, and FIG. 5*c* are respectively a schematic view of a three-dimensional, a side view, and a top view of the driving unit 100, and the top view direction of FIG. 5*c* is the direction indicated by the arrow in FIG. 5*b*, while the side view direction of FIG. 5*b* is the direction shown by the arrow in FIG. 5*c*.

In the embodiment of the present invention, the two driving arms 110 on one side of the driving unit 100 are installed up and down. Here, the up and down settings refer to the up and down positional relationship representations shown in FIG. 5*b*. Specifically, the two driving arms 110 (such as 110*a* and 110*b*) on the side of the driving unit 100 can be seen in the side view FIG. 5*b*, and in the top view FIG. 5*c*, 110*b* and 110*d* are blocked by 110*a* and 110*c*, respectively, wherein 110*b* and 110*d* are indicated by dotted lines in FIG. 5*c*.

In the embodiment of the present invention, since the driving wheel 130 is circular, the surfaces on which the adjacent teeth are applied with the engaging force are not parallel. Therefore, in order to keep the angle between the driving arms 110 and the teeth engaging surface 90 degree during engaging, thereby improving the engaging efficiency of the driving arms 110, when the driving arms 110 on one side of the driving unit 100 engage the wheel teeth 131, the lines representing the engaging directions of the two driving arms 110 intersect each other. Specifically, as shown in FIG. 5*b*, when the wheel teeth 131 are engaged by 110*a* and/or 110*b*, the straight line where 110*a* is located is $l_1$, the straight line where 110*b* is located is $l_2$, wherein the angle between $l_1$ and $l_2$ is $\alpha$, $3.1° \leq \alpha \leq 4.1°$. Specifically, in the embodiment of the present invention, $\alpha$=3.50. In another embodiment of the invention, $\alpha$=3.3°. In still another embodiment of the invention, $\alpha$=3.9°.

It should be noted that, in other embodiments of the present invention, according to different structural designs, when the driving arms 110 on one side of the driving unit 100 engage the wheel teeth 131, the lines representing the engaging directions of these two driving arms 110 can also be parallel ($\alpha$=0°) or skew with a structure also able to drive the driving wheel 130 to rotate to achieve the purpose of drug infusion. In this case, the angle $\alpha$ between $l_1$ and $l_2$ may be set according to the actual structure, such as according to the diameter, number of the driving wheel 130, the number of the wheel teeth 131, the pitch of the screw 170, the positional relationship and the number of the driving arms 110. For example, a may be between 0°~3.1° or $4.1° < \alpha \leq 7°$, and is not specifically limited herein.

Figure 6A:
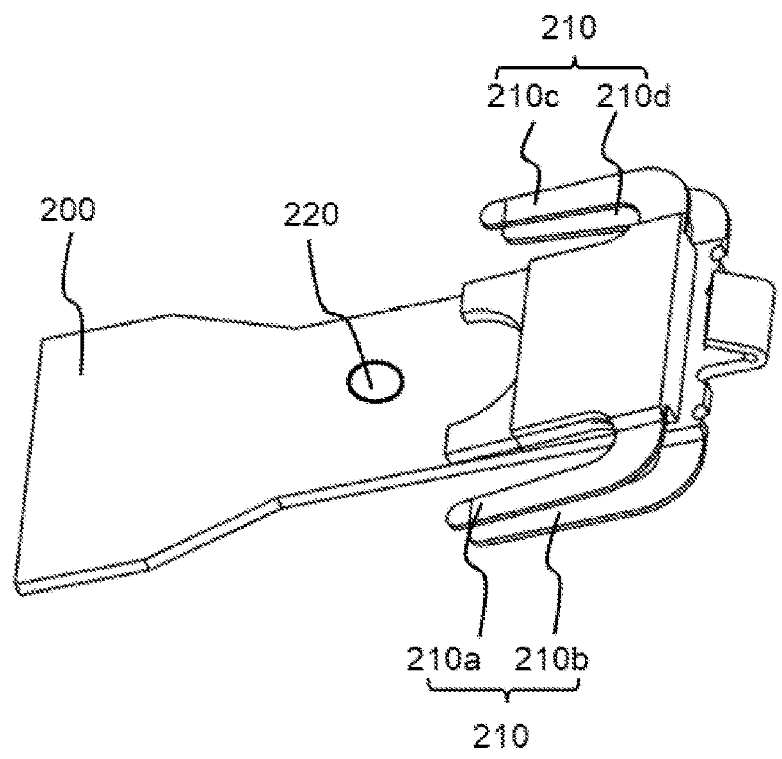
FIG. 6*a*-FIG. 6*b* are schematic structural view of a driving unit of a bilaterally driven intelligent control infusion device according to another embodiment of the present invention.
Figure 6B:
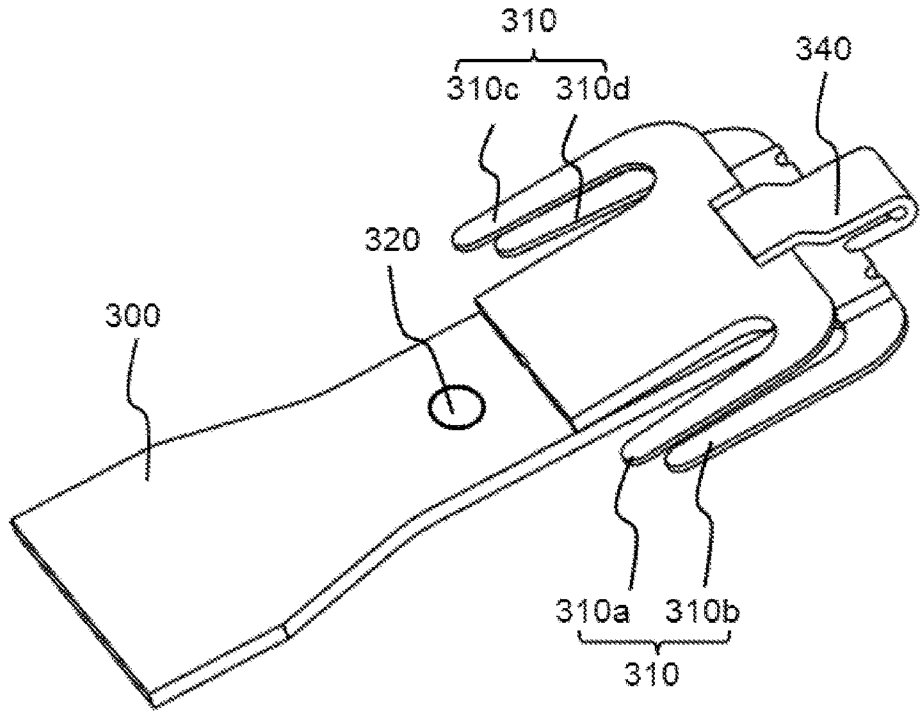

As shown in the dotted portion 20 of FIG. 5*a* and FIG. 5*b*, in the embodiment of the present invention, the two driving arms 110 on one side of the driving unit 100 are formed by folding at the dotted circle 20. In other embodiments of the present invention, the two driving arms 110 on one side of the driving unit 100 may also be formed by other means. As shown in the perspective view of the driving unit shown in FIG. 6*a* and FIG. 6*b*, the up position 210*a*, 210*c* and the down position 210*b*, 210*d* are respectively set in different structural subunits. As in FIG. 6*a*, the two structural subunits are secured together by welding or other means of attachment to form one single structure. And as shown in FIG. 6*b*, the two structural subunits are connected at the top position 340 of the driving unit 300, and then the top position 340 of the driving unit 300 is folded over to form the structure of the driving arms 310 in the embodiment of the present invention.

It should be noted that, in other embodiments of the present invention, the driving arms may be formed by other means, as long as the arms are able to drive the driving wheel to rotate, and is not specifically limited herein.

Figure 7:
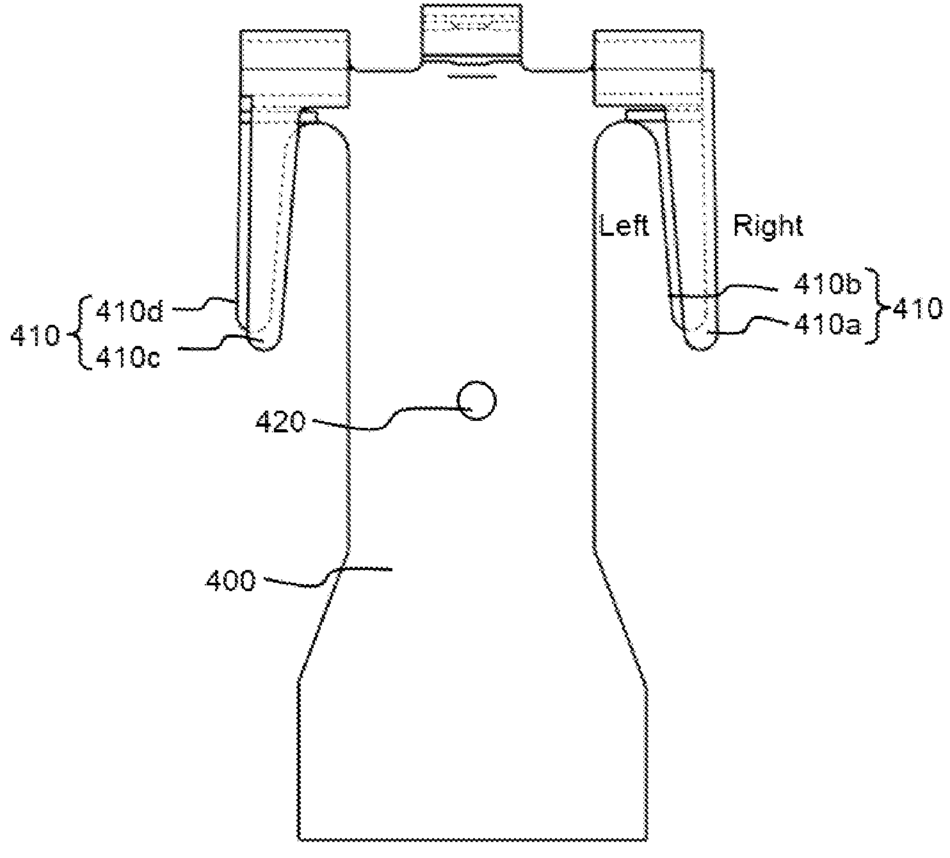
FIG. 7 is a schematic structural view of a driving unit in a bilaterally driven intelligent control infusion device according to another embodiment of the present invention.

Please refer to FIG. 7, which is a top view of a driving unit 400 according to another embodiment of the present invention.

The angles of view of FIG. 7 and FIG. 5*c* are the same. According to FIG. 5*a*, FIG. 5*b*, FIG. 5*c* and FIG. 4, it is apparent that the two driving arms on one side of the driving unit 400 are slightly offset from left and right, such as 410*a*, 410*b* and 410*c*, 410*d*. Specifically, in one embodiment of the invention, 410*a* and 410*c* are offset to the right and 410*b* and 410*d* are offset to the left.

It should be noted that, in other embodiments of the present invention, the left and right offset degree of the two driving arms on the same side and the direction in which the two are offset relative to each other need to be determined according to the actual structural design, and are not limited specifically described herein. Furthermore, in an embodiment of the invention, the two driving arms on one side of the driving unit can also be installed left and right. Here, the left and right installing mean that from the perspective of FIG. 7 (top view), two complete driving arms on one side of the driving unit can be seen, while from the perspective of FIG. 5*b* (side view), the driving arms close to the main body of the driving unit is completely or partially blocked by the driving arms away from driving unit's main body. In this case, the lines presenting the engaging directions of driving arms on the same side of driving unit is coplanar or skew. At the same time, there is no particular limitation on the length or the length relationship among different driving arms.

Figure 8:
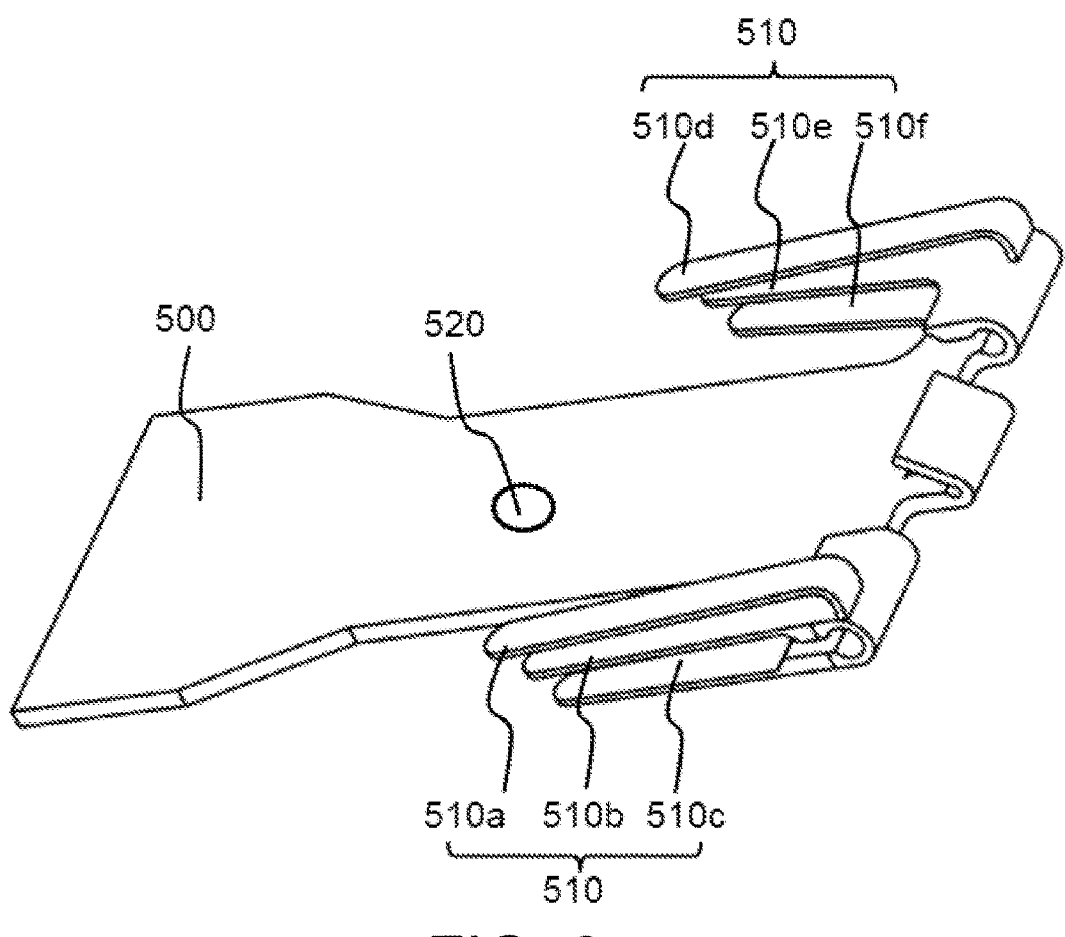
FIG. 8 is a schematic structural view of a driving unit in a bilaterally driven intelligent control infusion device according to another embodiment of the present invention.

Please refer to FIG. 8, which is a schematic perspective view of a driving unit 500 according to still another embodiment of the present invention.

Specifically, the driving unit 500 includes six driving arms 510, each three of which are installed on one side of the driving unit 500. Specifically, 510*a*, 510*b*, and 510*c* are installed on one side, and 510*d*, 510*e*, and 510*f* are installed on the other side. As described above, the lengths, the length relationships and the positional settings of the driving arms 510 on the same side are designed according to the specific structure and working principle, and are not specifically limited herein. Specifically, in the embodiment of the present invention, the positional relationship of the three driving arms 510 on the same side of the driving unit 500 is similar to that in FIG. 5*a*, FIG. 5*b* and FIG. 5*c*, that is, the three driving arms 510 on the same side of the driving unit 500 are installed up and down.

It should be noted that, in other embodiments of the present invention, the total number of driving arms may also be an odd number, such as three, five or more, that is, the numbers of driving arms on both sides of the driving unit are not equal. Moreover, the structural relationship between the different driving arms can be similar to that described above, and no specific restrictions are imposed here.

Referring to FIG. 6 and FIG. 5*c* together, FIG. 6 is a partial structural diagram of the driving wheel 130, and wheel teeth 131.

In the perspective of FIG. 5*c*, the horizontal distance between the driving ends of the two driving arms on one side of the driving unit 100 is h, and the pitch of the wheel teeth 131 is s, then 0.5 s≤h≤1.5 s. Specifically, in the embodiment of the present invention, h=0.8 s. In another embodiment of the invention, h=1.2 s. In still another embodiment of the invention, h=s. Here, the driving end of the driving arms 110 refers to the end of the driving arms 110 that directly contacts the wheel teeth 131 when engaged. The horizontal distance refers to the distance between two projection points of the driving ends of the two driving arms 110 on the same side of the driving unit 100 on a plane when viewed in an angle as shown in FIG. 5*c*.

It should be noted that in other embodiments of the present invention, 0.1 s≤h<0.5 s or 1.5 s<h≤2.5 s may be used, and the effects of the present invention may be also achieved, and also are not specifically limited herein.

As shown in FIG. 9, in the embodiment of the present invention, the driving wheel 130 is a ratchet, and the wheel teeth 131 are ratchet teeth. Each ratchet tooth surface includes a gentle surface and a steep surface, therefore it's easy to be engaged, as shown in FIG. 6. Moreover, in the embodiment of the present invention, the driving arms 110 of the driving unit 100 include a portion that drives the driving wheel 130 to rotate and a portion that does not drive the driving wheel 130 to rotate during the entire pivot of the driving unit 100 in one direction. The portion that drives the driving wheel 130 to rotate applies the engaging force on the steep surface of the ratchet teeth, in order to drive the driving wheel 130 to rotate in the C direction.

Please refer to FIG. 10, which is a schematic perspective view of the driving unit 100 and the driving wheel 130.

With reference to FIG. 10, FIG. 1, FIG. 5*b* and FIG. 5*c*, in the embodiment of the present invention, under the action of the power unit 180, the driving unit 100 pivots around the pivot shaft 120, thereby driving the plurality of driving arms 110 on both sides of the driving unit 100 to engage the wheel teeth 131 for rotation of the driving wheel 130.

Figure 11:
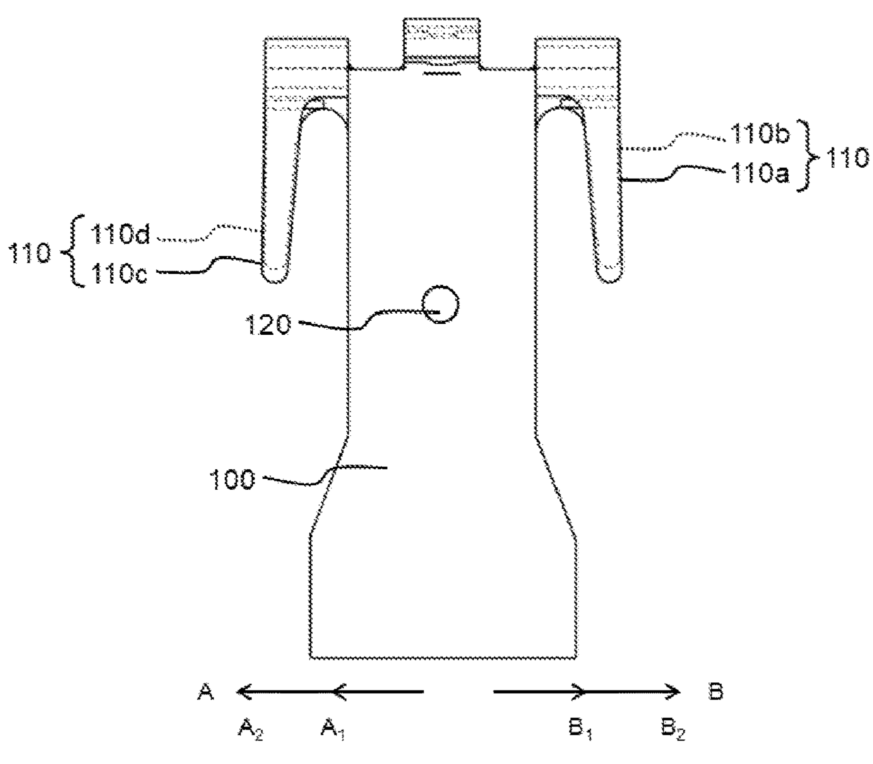
FIG. 11 is a schematic structural view showing a pivoting position of different movement modes of a driving unit in a bilaterally driven intelligent control infusion device according to an embodiment of the present invention.

Referring to FIG. 10 and FIG. 11 together, FIG. 8 is a schematic structural diagram of the adjustable pivoting movements of the driving unit 100

As described above, the driving unit 100 has a certain distance h between the driving ends of the driving arms 110 on the same side, and there is a certain angle α between the lines representing the driving directions when the arms are engaged. And therefore, the driving unit 100 pivots in one direction in a single time throughout the process, as shown in FIG. 10 in a single pivot in the direction A, 110*a* and/or 110*b* engage the wheel teeth 131 to drive the driving wheel 130, while 110*c* and 110*d* can slide on the wheel teeth 131 (as on the gentle surface of the ratchet teeth, but not exert a force for driving the driving wheel 130 to rotate). And obviously, 110*c* slides to the next driving position first. Here, the driving position refers to the position where the driving arm can engage the wheel teeth to advance, so as to the following driving position. At this time, the driving end of 110*c* acts on the steep surface of the ratchet teeth. At this time, the driving unit 100 stops pivoting and the driving arms 110*a* and/or 110*b* stop engaging the wheel teeth 131, and the driving wheel 130 stops rotating. Thus the driving unit 100 completes one step of pivot. Referring to FIG. 11, the driving unit 100 pivots in the A direction to reach $A_1$ position, which corresponds to one kind of pivot amplitude, making the infusion device have an infusion increment. The next moment the driving unit 100 continues to pivot in the A direction, 110*d* will slide to the next driving position. Similarly, the driving end of 110*d* also acts on the steep surface of the ratchet teeth. Thus the driving unit 100 completes a second step of pivot. Referring to FIG. 8, the driving unit 100 still pivots in the A direction to reach $A_2$ position, which corresponds to another kind of pivot amplitude, making the infusion device have another infusion increment. At this time, 110*c* and 110*d* respectively complete the sliding between adjacent wheel teeth 131, and the driving unit 100 completes the whole process of single pivot in the A direction, reaching $A_1$ and $A_2$ positions respectively, thereby driving the driving wheel 130 to rotate by two steps, realizing two-step infusion of the drug device and making the infusion device have two different infusion increments. It should be noted that, in the above pivoting process, 110*d* may first slide to the next wheel teeth 131, and then 110*c* slide to the next wheel teeth 131, which is not specifically limited herein. Similarly, when the driving unit 100 pivots in the B direction, it can reach $B_1$ and $B_2$ positions respectively, which also corresponds another two infusion increments.

Obviously, in the whole process of the above-mentioned single pivot in the A direction, the driving unit 100 undergoes an alternate action of pivot and stop, and the driving arms 110 alternately engage and stop engaging wheel teeth 131 to drive the driving wheel 130 to rotate and stop rotating, realizing two-step rotation of the driving wheel, and finally achieves two-level increment-adjustable drug infusion.

Specifically, when the driving unit has two driving arms on one side, the driving unit undergoes two-step movement of the pivot-stop-pivot-stop during the single pivot in the A direction, in order to drive driving wheel for two-step rotation. When the driving unit has three driving arms on one side, the driving unit performs the pivot-stop-pivot-stop-pivot-stop three-step motion in the whole process of single pivot in the A direction, realizing three-step rotation of the driving wheel to achieve three-level increment-adjustable drug infusion. By analogy, when there are more driving arms on one side of the driving unit, the driving unit realizes multiple-step driving of the driving wheel by the multiple-step actions of the pivot-stop-pivot-stop-pivot- . . . -pivot-stop, completing multi-level increment-adjustable drug infusion.

With continued reference to FIG. 10, in combination with the above, in the embodiment of the present invention, when the driving unit 100 drives the driving wheel 130 to rotate, at least one of the driving arms 110 on the driving force side applies an engaging force to the wheel teeth 131. While one or both of the driving arms 110 on the other side are in contact with the wheel teeth 131 without applying any force to the wheel teeth 131 to drive the driving wheel 130 to rotate. Therefore, there is a case in the embodiment of the present invention that only one of the driving arms 110 of the driving unit 100 engages the wheel teeth 131 to rotate the driving wheel 130, and the other driving arms 110 are in contact with the driving wheel 130 without applying any force to the wheel teeth 131 to rotate the driving wheel 130.

It should be noted that, in the embodiment of the present invention having three or more driving arms on one side of the driving unit, when the driving unit is in operation, the above-mentioned similar situation may also occur. When there are an odd number of driving arms, the numbers of driving arms on both sides of the driving unit are not equal, and the same process as above is also performed in the whole process of the driving unit rotating in a certain direction.

Referring to FIG. 11 again, in another embodiment of the present invention, when the driving unit 100 has two driving arms 110 on one side, the driving unit 100 pivots one step in the A direction, that is, reaching the $A_1$ position, and then pivots one or two steps in the B direction, that is, reaching the $B_1$ or $B_2$ position until the pivot in the B direction stops, the driving unit 100 pivoting by different amplitudes. This process completes the alternate pivot of the driving unit 100 in two directions, so that the driving wheel 130 can be rotated in multiple steps. Therefore, in the embodiment of the present invention, the driving unit 100 can alternately switch modes among $A_1$-$B_1$ or $A_1$-$B_1$-$B_2$ or $B_1$-$A_1$-$A_2$, so as to achieve the purpose of switching among different increments of infusion.

With continued reference to FIG. 11, in another embodiment of the present invention, the driving unit 100 can also be pivoted directly to the $A_2$ position without passing through the $A_1$ position, then directly pivoted to the $B_2$ position without passing through the $B_1$ position, that is, the driving unit 100 alternately pivots between the $A_2$-$B_2$ positions. As described above, the driving unit 100 can also alternately pivot between the $A_1$-$B_1$ positions. Obviously, in a unit time, the dosage of infused drug when the driving unit 100 alternately pivots between the $A_2$-$B_2$ positions is greater than the dosage of infused drug when it alternately pivots between the $A_1$-$B_1$ positions.

In other embodiments of the present invention, as shown in FIG. 11, after the driving unit 100 pivots in the direction A and the driving arm 110*c* or 110*d* slides to the driving position, the driving unit 100 may continue to pivot in the direction A until both the driving arm 110*c* and 110*d* are away from the driving position, the driving unit 100 stopping pivoting and starting to pivot in the B direction at the next moment. This operation mode enables the driving unit 100 to have more kinds of movement amplitudes, that is, multiple-mode pivot. Obviously, when the driving unit 100 pivots in the direction B for a certain period of time, all the driving arms 110 slide on the surface of the wheel teeth 131, that is, no engaging is performed. For ease of description, the above process will be described in detail below in conjunction with an embodiment in which the driving unit 100 includes only two driving arms.

Figure 12A:
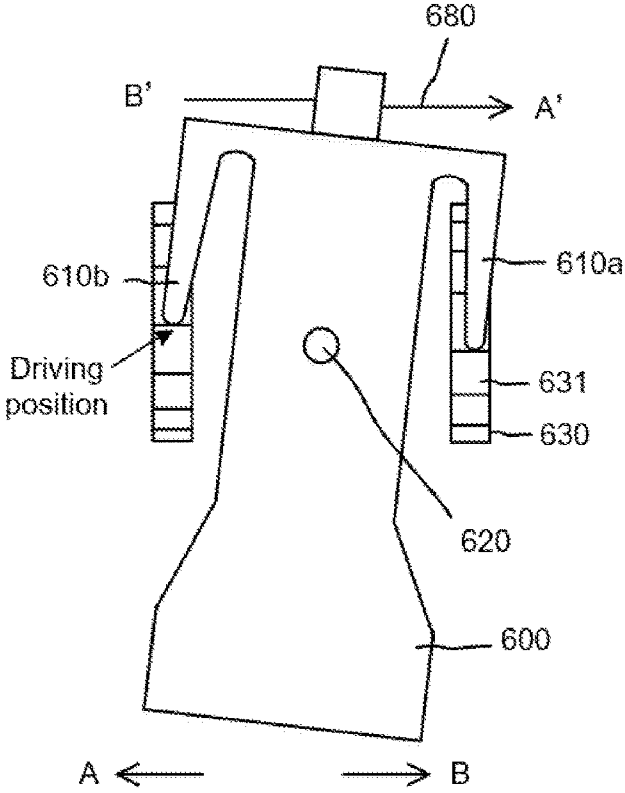
FIG. 12*a*-FIG. 12*c* are schematic structural views of a driving unit including two driving arms in a bilaterally driven intelligent control infusion device according to an embodiment of the present invention.
Figure 12B:
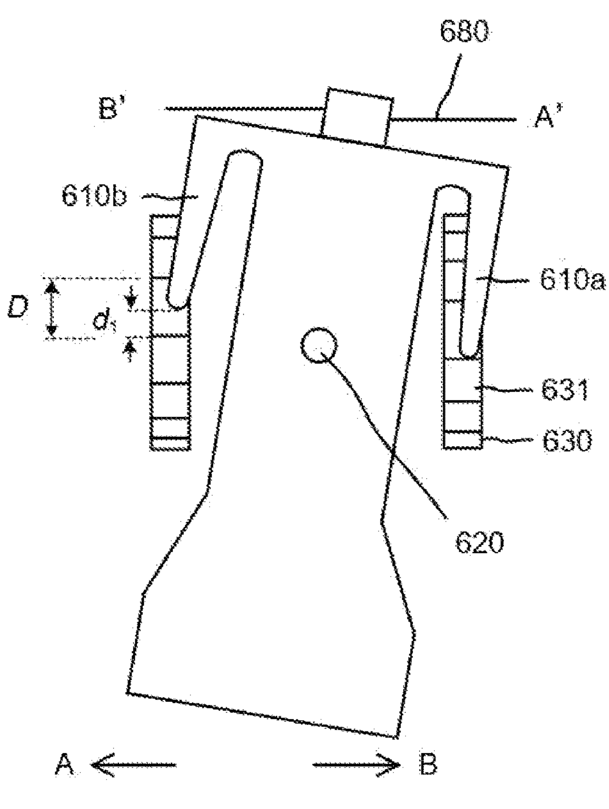
Figure 12C:
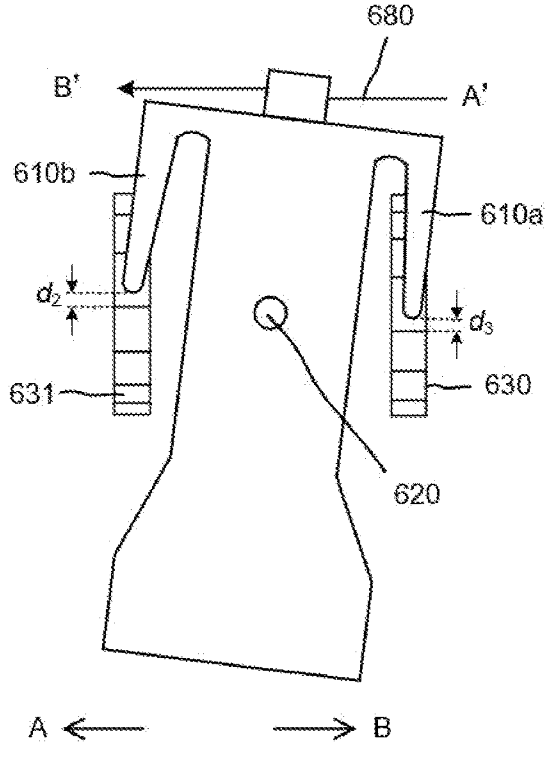

FIG. 12*a*-FIG. 12*c* are schematic structural views of the driving unit 600 including two driving arms 610*a* and 610*b*.

Similar to the driving principle described above, in one embodiment of the present invention, when the power unit 680 applies force to the driving unit 600 in the A' direction, the driving arm 610*a* engages the wheel teeth 631 forward, making the driving unit 600 pivot around the pivot shaft 620 and the driving arm 610*b* sliding on the surface of the wheel teeth 631 until the driving arm 610*b* reaches the driving position, in which the driving unit 600 pivots by a certain amplitude, as shown in FIG. 12*a*. The power unit 680 starts to apply force in the B' direction, making the driving arm 610*b* engage the wheel teeth 631 forward. By analogy, the driving unit 600 alternately pivots in two directions.

In the embodiment of the present invention, after the driving arm 610*b* reaches the driving position, the driving unit 600 continues to pivot in the direction A, thus the driving arm 610*b* continuing to slide on the surface of the wheel teeth 631. After the distance between the driving end of the driving arm 610*b* and the steep surface of the wheel teeth 631 is $d_1$, the power unit 680 stops outputting force, which is shown in FIG. 12*b*. At this time, the driving unit 600 pivots by a larger amplitude. If the pitch of the wheel tooth is D, then $d_1=D/n$, $n>1$. Obviously, after the power unit 600 outputs force in the direction of B', both the driving arms 610*b* and 610*a* slide on the surface of the wheel teeth 631 within a period of time after the driving unit 600 starts to pivot, as shown in FIG. 12*c*. The distances between the driving arms 610*b*, 610*a* and the steep surfaces of their corresponding wheel teeth 631 are $d_2$ and $d_3$, respectively. Obviously, $d_2<D$ and $d_3<D$. As described above, when more driving arms are provided on the driving unit 600, a similar situation will occur for each driving arm.

The total distance of the driving arm 610*b* sliding in the above process can be arbitrarily selected, for example, the total sliding distance is 0.4D, 0.7D, D (as shown in FIG.

12*a*), 1.5D, 1.75D, 2D, 2.3D, 2.5D, etc. The driving unit 600 has various pivot amplitudes, that is, various rotation gears, making the infusion device have multiple infusion increments.

Figure 13A:
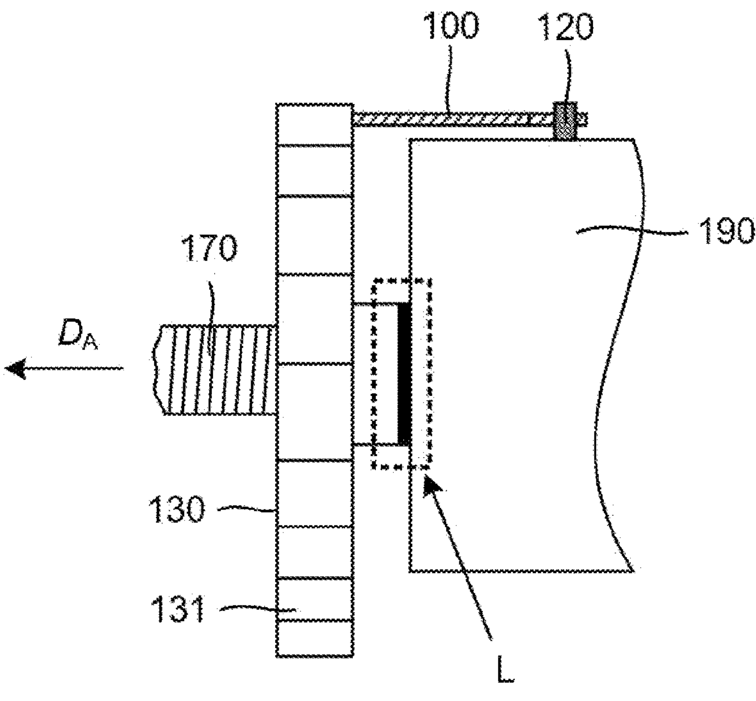
FIG. 13*a*-FIG. 13*b* are schematic structural views of a driving wheel and a base or a limiting member in a bilaterally driven intelligent control drug infusion device according to an embodiment of the present invention.
Figure 13B:
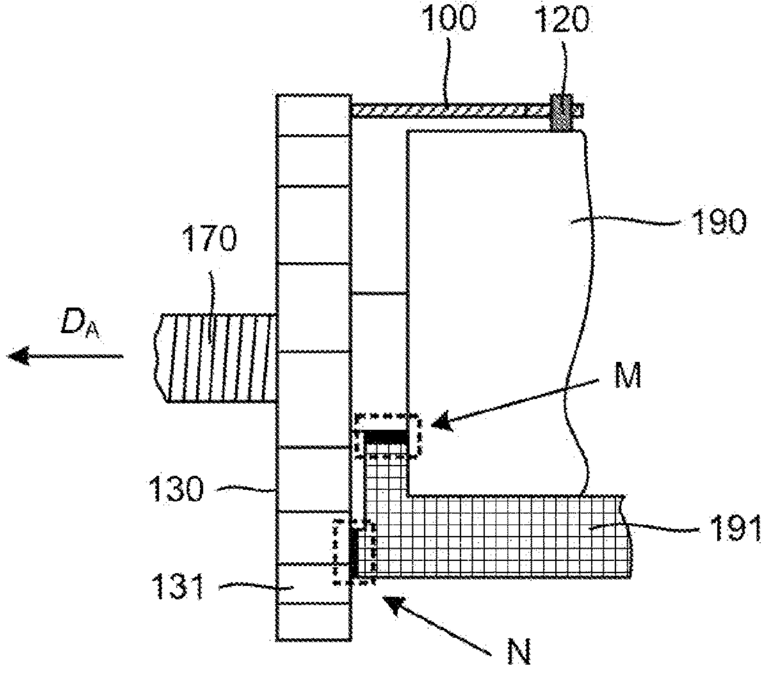

FIG. 13*a* and FIG. 13*b* are schematic diagrams of the driving wheel 130 and the base 190, or the position limited member 191 according to an embodiment of the present invention. FIG. 13*a* and FIG. 13*b* are front views of partial structures in FIG. 1.

When the driving arm 110 slides on the surface of the wheel teeth 131, the driving arm 110, contact with the wheel teeth 131, applies a certain pressure to the driving wheel 130 to ensure the non-rotating of the driving wheel 130. However, it is obvious that due to the structural features of the wheel teeth 131 and the circumference of the driving wheel 130, the pressure applied by the driving arm 110 is not equal at different positions. Therefore, when the driving arm 110 slides (including reset movement or sliding forward) on the surface of the wheel teeth 131, the driving wheel 130 may rotate forward or reverse, which affects the accuracy of the drug infusion volume and brings safety risk.

As shown in FIG. 13*a*, the driving wheel 130 is movably assembled on the base 190 remaining in frictional engagement. Here, the friction fit between these two means a certain friction force preset between two mutually moving structures, so as to the meaning of the following friction fit. In the embodiment of the present invention, the frictional force of the relative movement between the driving wheel 130 and the base 190 is applied or increased at the position L, indicated by the dotted frame, to ensure that when the driving arm 110 slides on the surface of the wheel teeth 131, the driving wheel 130 stops rotating.

As shown in FIG. 13*b*, in another embodiment of the present invention, the infusion device further includes a position limited member 191 that is movably assembled on the base 190 to limit the position of the driving wheel 130. The position limited member 191 is in friction fit with the driving wheel 130 at position M or position N, indicated by the dotted frame. Similarly, in the embodiment of the present invention, the position limited member 191 increases the frictional force that the driving wheel 130 receives when rotating, also ensuring that the driving wheel 130 stops rotating when the driving arm 110 slides on the surface of the wheel teeth 131. At the same time, the position limited member 191 can make full use of the internal space of the infusion device, and frictionally cooperate with the driving wheel 130 at multiple positions.

Other embodiments of the present invention do not limit the position of the above friction fit, as long as the condition for applying or increasing the friction force received by the second driving unit during movement is satisfied. For example, the friction force can also be applied on both sides of the driving wheel 130 at the same time. The embodiment of the present invention neither limits the material of the position limited member 191. For example, the position limited member 191 is an elastic member, a plastic member or a metal member.

Other embodiments of the present invention may increase the pressure of the driving arm 110 on the wheel teeth 131 instead of providing the above-mentioned friction fit, which can increase the maximum static friction of the driving wheel 130 and also ensure the non-rotating of the driving wheel 130 when the driving arm 110 slides on the surface of the wheel teeth 131.

If the minimum dosage of infused drug driven by the driving unit is the minimum increment of the infusion device, the bilaterally driven intelligent control infusion device using the embodiment of the present invention can reduce the minimum increment of drug dosage and achieve more precise control of the drug infusion. When the patient needs to infuse more drugs, the large $A_2$-$B_2$ mode can be selected to speed up the infusion rate. When a small amount of drug needs to be infused, the patient or artificial pancreas can select the small $A_1$-$B_1$ mode to reduce the drug infusion rate and achieve precise control of the drug infusion.

Compared with the device with increment-unadjustable infusion, in the bilaterally driven intelligent control infusion device, the driving unit performs multiple-mode operation, making the infusion device have multiple infusion increments or infusion rates. With the bilaterally driven intelligent control infusion device of the embodiment of the invention, the patient or artificial pancreas can freely and flexibly switch between different increments of infusion according to the actual drug dosage and the demand of the infusion rate, thereby improving the infusion efficiency. At the same time, intermediate $A_1$-$B_1$-$B_2$ mode or $B_1$-$A_1$-$A_2$ mode and the small $A_1$-$B_1$ mode are set along with the large $A_2$-$B_2$ mode. And the bilaterally driven intelligent control infusion device can reduce the minimum dosage of infused drug in order to achieve the goal of precise control of the infusion.

As with the bilaterally driven intelligent control infusion device of the embodiment of the present invention, when the infusion is started, the amount of drug required is relatively large, and the patient can select the large $A_2$-$B_2$ mode shown in FIG. 11 for infusion. After a period of infusion, the intermediate $A_1$-$B_1$-$B_2$ mode or $B_1$-$A_1$-$A_2$ mode can be used to reduce the rate of drug infusion. When the drug infusion is about to be completed, the patient can switch to the small $A_1$-$B_1$ mode to further reduce the infusion rate and achieve precise control of the drug infusion. Of course, the patient can also choose one or several of the modes for infusion, and there are no specific restrictions.

In other embodiments of the present invention, when more than two driving arms are installed on one side of the driving unit, the infusion device can have more and more elaborate infusion modes, and the patient can further flexibly control the infusion to make the infusion process more precisely.

Figure 14:
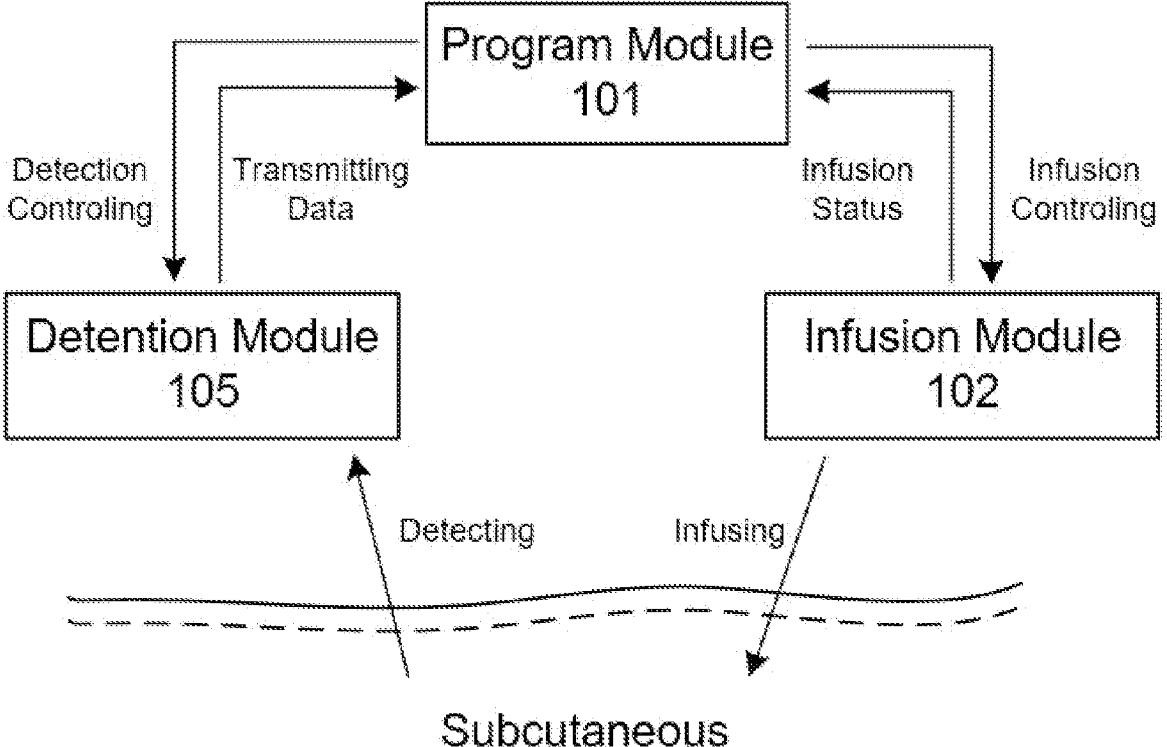
FIG. 14 is a schematic view of the module relationship of the closed-loop artificial pancreas according to one embodiment of the present invention.

FIG. 14 is a schematic view of the module relationship of the closed-loop artificial pancreas according to one embodiment of the present invention.

The closed-loop artificial pancreas disclosed in the embodiment of the present invention comprises the above mentioned bilaterally driven intelligent control infusion device; and a detection unit 105, connected with the program unit and infusion unit of the infusion device, configured to detect blood glucose continuously. In one embodiment of the present invention, the detection unit 105 is a Continuous Glucose Monitoring (CGM) for detecting real-time BG, monitoring BG changes, and also sending them to the program unit 101.

The program unit 101 is used to control the detection unit 105 and the infusion unit 102. Therefore, the program unit 101 is connected to the detection unit 105 and the infusion unit 102, respectively. Here, the connection refers to a conventional electrical connection or a wireless connection.

The infusion unit 102 includes the essential mechanical structures used to infuse insulin and controlled by the program unit 101, which will be described in detail below. According to the current insulin infusion dose calculated by the program unit 101, the infusion unit 102 injects the currently insulin dose required into the user's body. At the same time, the real-time infusion status of the infusion unit 102 can also be fed back to the program unit 101.

The embodiment of the present invention does not limit the specific positions and connection relationships of the detection unit 105, the program unit 101 and the infusion unit 102, as long as the aforementioned functional conditions can be satisfied.

As in an embodiment of the present invention, the three are electrically connected to form a single structure. Therefore, the three modules can be attached together on only one position of the user's skin. If the three modules are connected as a whole and attached in the only one position, the number of the device on the user skin will be reduced, thereby reducing the interference of more attached devices on user activities. At the same time, it also effectively solves the problem of the poor wireless communication between separating devices, further enhancing the user experience.

As in another embodiment of the present invention, the program unit 101 and the infusion unit 102 are electrically connected to each other to form a single structure while the detection unit 105 is separately provided in another structure. At this time, the detection unit 105 and the program unit 101 transmit wireless signals to each other to realize mutual connection. Therefore, the program unit 101 and the infusion unit 102 can be attached on the same position of the user's skin while the detection unit 105 is attached on the other position.

As in another embodiment of the present invention, the program unit 101 and the detection unit 105 are electrically connected to each other forming a single structure while the infusion unit 102 is separately provided in another structure. The infusion unit 102 and the program unit 101 transmit wireless signals to each other to realize mutual connection. Therefore, the program unit 101 and the detection unit 105 can be attached on the same position of the user's skin while the infusion unit 102 is attached on the other position.

As in another embodiment of the present invention, the three are respectively provided in different structures, thus being attached on different position. At this time, the program unit 101, the detection unit 105 and the infusion unit 102 respectively transmit wireless signals to each other to realize mutual connection.

It should be noted that the program unit 101 of the embodiment of the present invention also has functions such as storage, recording, and access to the database, thus, the program unit 101 can be reused. In this way, not only can the user's physical condition data be stored, but also the production cost and the user's consumption cost can be saved. As described above, when the service life of the detection unit 105 or the infusion unit 102 expires, the program unit 101 can be separated from the detection unit 105, the infusion unit 102, or both the detection unit 105 and the infusion unit 102.

Generally, the service lives of the detection unit 105, the program unit 101 and the infusion unit 102 are different. Therefore, when the three are electrically connected to each other to form a single device, the three can also be separated from each other in pairs. For example, if one module expires firstly, the user can only replace this module and keep the other two modules continuous using.

Here, it should be noted that the program unit 101 of the embodiment of the present invention may also include multiple sub-modules. According to the functions of the sub-modules, different sub-modules can be respectively assembled in different structure, which is not specific limitation herein, as long as the control conditions of the program unit 101 can be satisfied.

In summary, the present invention discloses a bilaterally driven intelligent control infusion device and a closed-loop artificial pancreas, can be operated with multiple infusion rate, which improves the flexibly of the infusion process, and the driving unit performs multiple-mode operations, thereby making the infusion device have multiple infusion increments or infusion rates, realizing increment-adjustable drug infusion, increasing the patient's flexibility in controlling the infusion process and improving the efficiency of drug infusion. At the same time, the bilaterally driven intelligent control infusion device also reduces the minimum dosage of infused drug, from which the patients can accurately control the drug infusion and precisely manage their own physiological condition.

While the invention has been described in detail with reference to the specific embodiments of the present invention, it should be understood that it will be appreciated by those skilled in the art that the above embodiments may be modified without departing from the scope and spirit of the invention. The scope of the invention is defined by the appended claims.

What is claimed is:

1. A bilaterally driven intelligent control infusion device, comprising:

an infusion unit, the infusion unit comprises a drug storage unit, a piston and a rigid screw, the piston is arranged in the drug storage unit, a metal piece arranged on the piston, fixedly connected to the rigid screw;

a driving wheel, provided with wheel teeth, drives the rigid screw to move by rotation, the rigid screw advances the piston to move;

a driving unit cooperating with the driving wheel;

a power unit, connected to the driving unit, outputs forces in two different directions on the driving unit to lead the driving unit to pivot;

a position detector, interacting with the metal piece to generate a signal;

a program unit, connected to the infusion unit, converts the signal into a position information of the piston and controls the driving unit to operate with a different infusion rate according to requirements, wherein the program unit controls the driving unit to perform a multiple-mode operation, making the infusion device have multiple infusion increments or infusion rates, wherein the multiple-mode operation of the driving unit includes multiple different movement amplitudes and multiple different movement rates in a unit time, wherein the multiple different movement amplitudes include controlling a magnitude of a current of the power unit by the program unit to rotate the driving unit in a first direction to a first position or controlling the magnitude of the current of the power unit by the program unit to rotate the driving unit in the first direction to a second position, wherein the first position is different from the second position.

2. The bilaterally driven intelligent control infusion device of claim 1, wherein the rigid screw is a metal screw, and the metal piece is electrically connected with the metal screw, so that the metal piece and the position detector constitute a capacitor, and a linear movement of the metal piece causes a change in capacitance making the position detector generate the signal, wherein the signal is an electrical signal.

3. The bilaterally driven intelligent control infusion device of claim 1, wherein the metal piece is a magnetic metal piece, and the position detector is a magnetic induction detector, a linear movement of the magnetic metal piece causes a change in a magnetic field around the position detector making the position detector generate the signal, wherein the signal is a magnetic signal.

4. The bilaterally driven intelligent control infusion device of claim 1, further comprising:

a pivot shaft, and the driving unit includes at least two driving arms, and the driving unit pivots around the pivot shaft to drive the driving arms to move.

5. The bilaterally driven intelligent control infusion device of claim 4, wherein the driving wheel includes at least two sub-wheels, and the driving arms rotate the driving wheel by engaging the wheel teeth.

6. The bilaterally driven intelligent control infusion device of claim 5, wherein the pivot shaft is disposed between the two sub-wheels, one or more of the driving arms are respectively disposed on both sides of the driving unit, and each sub-wheel cooperates with at least one of the driving arms.

7. The bilaterally driven intelligent control infusion device of claim 6, wherein one of the multiple different movement amplitudes corresponds to one kind of pivot mode of the driving unit, and the driving unit, pivoting in various pivot modes, drives the driving arm to rotate the driving wheel to implement increment-adjustable infusion, and each increment-adjustable infusion corresponds to one of the multiple infusion increments.

8. The bilaterally driven intelligent control infusion device of claim 7, wherein the various pivot modes of the driving unit include: after pivoting one or more steps in the first direction in a single time, the driving unit starts pivoting one or more steps in a second direction until the end of the pivot in the second direction, the driving unit completes an alternate pivot in both of the first direction and the second direction to perform multiple-mode driving on the driving wheel.

9. The bilaterally driven intelligent control infusion device of claim 8, wherein the wheel teeth are ratchet teeth, and during a whole process of the driving unit pivoting in one of the first direction and the second direction, the driving unit alternately pivots and stops for multiple times to drive the driving arms to alternately engage and stop engaging the ratchet teeth, so that the driving wheel alternately rotates and stops rotation to perform the multiple-mode driving on the driving wheel.

10. The bilaterally driven intelligent control infusion device of claim 9, wherein when the driving unit drives the driving wheel, at least one of the driving arms on one side of the driving unit engages the wheel teeth, while the driving arm on a different side of the driving unit slide on a surface of the wheel teeth.

11. The bilaterally driven intelligent control infusion device of claim 10, further including a base on which the driving wheel is movably assembled, and the base and the driving wheel are frictionally fit, and the driving wheel stops rotating when the driving arm is sliding on the surface of the wheel teeth.

12. The bilaterally driven intelligent control infusion device of claim 11, further including a position limited member which is movably assembled on the base to limit the position of the driving wheel, and the position limited member and the driving wheel are frictionally fit, and the driving wheel stops rotating when all of the driving arms are sliding on the surface of the wheel teeth.

13. A closed-loop artificial pancreas, comprising:

the bilaterally driven intelligent control infusion device according to claim 1; and a detection unit, configured to detect blood glucose continuously, connected with the program unit and infusion unit of the infusion device.

14. The closed-loop artificial pancreas of claim 13, wherein any two of the detection unit, the program unit and the infusion unit are connected to each other configured to form a single structure whose attached position on a user's skin is different from a remaining one of the detection unit, the program unit, and the infusion unit.

15. The closed-loop artificial pancreas of claim 13, wherein the detection unit, the program unit and the infusion unit are connected together configured to form a single structure which is attached on only one position on a user's skin.

* * * * *